US007618589B2

(12) United States Patent
Toi et al.

(10) Patent No.: US 7,618,589 B2
(45) Date of Patent: Nov. 17, 2009

(54) AUTOMATIC DISPENSER

(75) Inventors: Hiroatsu Toi, Hitachinaka (JP); Kenji Yamada, Hitachinaka (JP); Masataka Morita, Hitachinaka (JP); Hidetaka Osawa, Hitachinaka (JP); Tadashi Ohkawara, Hitachinaka (JP)

(73) Assignee: Hitachi Koki Co., Ltd., Tokyo (JP)

( * ) Notice: Subject to any disclaimer, the term of this patent is extended or adjusted under 35 U.S.C. 154(b) by 714 days.

(21) Appl. No.: 11/116,299

(22) Filed: Apr. 28, 2005

(65) Prior Publication Data

US 2006/0051246 A1 Mar. 9, 2006

(30) Foreign Application Priority Data

Sep. 7, 2004 (JP) .......................... P2004-259489
Sep. 7, 2004 (JP) .......................... P2004-259490

(51) Int. Cl.
*B01L 3/02* (2006.01)

(52) U.S. Cl. .......................... 422/100; 422/50; 422/63; 422/931

(58) Field of Classification Search ................. 422/100, 422/50, 63, 64, 65, 66; 436/180, 137
See application file for complete search history.

(56) References Cited

U.S. PATENT DOCUMENTS 6,338,820 B1 * 1/2002 Hubbard et al. ............... 422/64
6,495,106 B1 * 12/2002 Kalra et al. ................. 422/100
6,599,479 B1 * 7/2003 Kietzmann et al. .......... 422/100
2002/0108857 A1 * 8/2002 Paschetto et al. ............ 204/457
2003/0075556 A1 * 4/2003 Tajima et al. ................. 222/23
2004/0208795 A1 * 10/2004 Toi et al. .................... 422/100

FOREIGN PATENT DOCUMENTS

| | | |
|---|---|---|
| EP | 1 243 929 | 9/2002 |
| EP | 1 333 288 | 8/2003 |
| JP | H05-079472 | 10/1993 |
| JP | H10-115620 | 5/1998 |
| JP | 11-295323 | 10/1999 |
| JP | 2001-183382 | 7/2001 |
| JP | 2001-330619 | 11/2001 |
| JP | 2004-170159 | 6/2004 |

OTHER PUBLICATIONS

Office Action in Japanese Pat. Appln. 2004-259490, dated Apr. 10, 2009; and English translation.

* cited by examiner

*Primary Examiner*—Jill Warden
*Assistant Examiner*—Jonathan M Hurst
(74) *Attorney, Agent, or Firm*—Antonelli, Terry, Stout & Kraus, LLP.

(57) ABSTRACT

An automatic dispenser includes a dispensing head, a transporter, a controller, sensors, and an adjustor. The dispensing head accommodates a plurality of dispensing tips and draws liquid into and ejects liquid from the dispensing tips. The transporter moves the dispensing head within an XYZ space. The controller controls drawing and ejecting of liquid by the dispensing head and movement of the dispensing head by the transporter. The sensors detect whether dispensing tips are mounted in the dispensing head. The adjustor aligns the reference positions of the dispensing head and the sensors in the XY plane.

10 Claims, 13 Drawing Sheets

AUTOMATIC DISPENSER

BACKGROUND OF THE INVENTION

1. Field of the Invention

The present invention relates to an automatic dispenser, and particularly to an automatic dispenser having an adjustable dispensing head and being capable of determining the shape and mounting status of dispensing tips in the dispensing head.

2. Description of the Related Art

Dispensing liquid samples, reagents, or the like to sample vessels in small quantities is an operation frequently performed during testing and analysis in the field of biochemistry. The dispensing operation is performed by drawing the liquid into and ejecting the liquid from dispensing tips mounted in a dispensing head. The dispensing tips are normally a disposable type that can be replaced with new dispensing tips after each use.

Recently, the number of these dispensing operations has increased dramatically in biochemical testing and analysis. When performed manually, however, the operations are inefficient and can lead to such problems as the user forgetting to mount or improperly mounting the dispensing tips. As a consequence, we are now seeing a shift from manual dispensing operations to automatic dispensing.

A conventional automatic dispenser includes a tip rack in which a plurality of dispensing tips are arranged, a dispensing head for accommodating the dispensing tips and dispensing the liquid contained therein, and sensors for determining the existence of dispensing tips in the tip rack. By monitoring the existence of dispensing tips in the tip rack, the sensors can determine whether a dispensing tip has been mounted in a dispensing nozzle. For example, the sensor determines that a mounting error has occurred when a dispensing tip that should have been mounted in a dispensing nozzle remains in the tip rack. Accordingly, the automatic dispenser can detect the mounting errors for mounting dispensing tips in the dispensing head, as described in Japanese unexamined patent application publication No. HEI-11-295323, for example.

However, if either the tip rack or the sensors deviate from their prescribed positions in the automatic dispenser of Japanese unexamined patent application publication No. HEI-11-295323, the sensors do not perform detection at the correct positions. For example, if the sensors are offset from their prescribed positions so that the sensors monitor a gap between dispensing tips, then the sensors determine that there are no remaining dispensing tips, that is, that all tips have been mounted.

Further, the automatic dispenser of Japanese unexamined patent application publication No. HEI-11-295323 can detect only whether all dispensing tips have been mounted properly in the dispensing head. Accordingly, this automatic dispenser cannot detect an abnormality when the dispensing tips are not correctly mounted in the dispensing head or when the mounted dispensing tips have a different shape. Hence, if the user mistakenly disposes a different type of dispensing tip in the dispensing rack, for example, the desired amount of reagent will not be acquired.

SUMMARY OF THE INVENTION

In view of the foregoing, it is an object of the present invention to provide an automatic dispenser capable of adjusting the position of the dispensing head and capable of determining the shape and mounting states of the dispensing tips.

This and other objects can be attained by an automatic dispenser that includes a dispensing head, a transporter, a controller, a sensor, and an adjustor. The dispensing head is movable within an XYZ space defined by X-axis, Y-axis and Z-axis extending perpendicular to one another and having a reference position. A plurality of dispensing tips is mountable on the dispensing head. A liquid is drawn into and ejected from at least one of dispensing tips mounted on the dispensing head. The transporter moves the dispensing head within the XYZ space by designating coordinate values of the X-axis, Y-axis and Z-axis. The controller controls drawing and ejecting the liquid by the dispensing head and the movement of the dispensing head by the transporter. The sensor is disposed in a position within the XYZ space, detects a mounting state of one or more dispensing tips mounted on the dispensing head when the dispensing head moves past a detection position, and outputs a mounting state signal indicative of the mounting state of one or more dispensing tips. The adjustor adjusts, based on the mounting state signal, at least one of X-axis, Y-axis and Z-axis coordinate values of the reference position.

The reference position is, for example, an origin of the XYZ space wherein a target position to which the dispensing head is moved by the transporter is changed when at least one of X-axis, Y-axis and Z-axis coordinate values of the reference position is adjusted by the adjuster.

With this construction, adjustments can be performed to align the reference position of the dispensing head and the sensor when the reference position is aligned in the XYZ space. Accordingly, dispensing tips mounted in the dispensing head can be detected with correct positions.

The controller may include a waveform display that displays a waveform of the mounting state signal output from the sensor. With this construction, a waveform showing positions of the dispensing tips is displayed on the waveform display.

The controller may further include a sensor adjustment display that prompts a user to adjust the position of the sensor based on the mounting state signal output from the sensor. With this construction, the controller may display a message on the sensor adjustment display indicating that the sensor is out of alignment when the sensor is offset from a prescribed position.

According to another aspect of the invention, there is provided an automatic dispenser that includes a dispensing head, a transporter, a controller, and a sensor. A plurality of dispensing tips is mountable on the dispensing head, and a liquid is drawn into and ejected from at least one of the dispensing tips mounted on the dispensing head. The transporter moves the dispensing head within an XYZ space defined by X-axis, Y-axis and Z-axis extending perpendicular to one another by designating coordinate values of the X-axis, Y-axis and Z-axis. The controller controls drawing and ejecting the liquid by the dispensing head and the movement of the dispensing head by the transporter. The sensor detects the dispensing tips which move with the dispensing head and generates a detection signal indicative of the detected dispensing tips. The controller includes a storage unit that stores a model waveform, and determines a shape and mounting states of the dispensing tips by comparing the detection signal with the model waveform.

The controller may further include a dispensing tip adjustment display that prompts a user to remount a dispensing tip when the shape of the dispensing tip is not a prescribed shape or when the dispensing tip is not perfectly mounted.

The sensor may include a plurality of the sensor elements that detect the dispensing tip at a plurality of locations. In this case, the controller determines the shape and mounting states of the dispensing tips based on a plurality of signals for the dispensing tip detected by the plurality of sensor elements.

The transporter may move the dispensing head so that the sensor can detect the dispensing tips at a plurality of locations. In this case, the controller determines the shape and mounting states of the dispensing tips based on signals for a plurality of locations on the dispensing tips detected by the sensor.

The transporter may include a head orientation changing device that changes an orientation of the dispensing head so that the sensor can detect a plurality of differing surfaces on the dispensing tips. In this case, the controller determines the shape and mounted states of the dispensing tips based on signals for the plurality of surfaces of the dispensing tip detected by the sensor.

The controller may further include a detected waveform display that generates a waveform based on the detection signal fed from the sensor and displays the waveform.

The model waveform indicates a predetermined ideal detection period, wherein the controller compares a detection period indicated by the waveform with the ideal detection period and determines the shape and mounting states of the dispensing tips.

BRIEF DESCRIPTION OF THE DRAWINGS

The particular features and advantages of the invention as well as other objects will become apparent from the following description taken in connection with the accompanying drawings, in which:

FIG. 4(*b*) is an explanatory diagram showing the detection ending position when the dispensing head is oriented longitudinally;

FIG. 5(*b*) is an explanatory diagram showing the detection ending position when the dispensing head is oriented latitudinally;

FIG. 6(*b*) is an explanatory diagram showing another example of a signal waveform displayed in the waveform window;

FIG. 6(*c*) is an explanatory diagram showing another example of a signal waveform displayed in the waveform window;

FIG. 6(*d*) is an explanatory diagram showing another example of a signal waveform displayed in the waveform window;

FIG. 7(*b*) is an explanatory diagram showing another example of a signal waveform displayed in the waveform window;

FIG. 7(*c*) is an explanatory diagram showing another example of a signal waveform displayed in the waveform window;

FIG. 8(*b*) is a explanatory diagram showing another example of a waveform window where a signal waveform is displayed;

FIG. 8(*c*) is a explanatory diagram showing another example of a waveform window where a signal waveform is displayed;

FIG. 8(*d*) is a explanatory diagram showing another example of a waveform window where a signal waveform is displayed;

FIG. 8(*e*) is a explanatory diagram showing another example of a waveform window where a signal waveform is displayed;

DETAILED DESCRIPTION OF THE PREFERRED EMBODIMENTS

Figure 1:
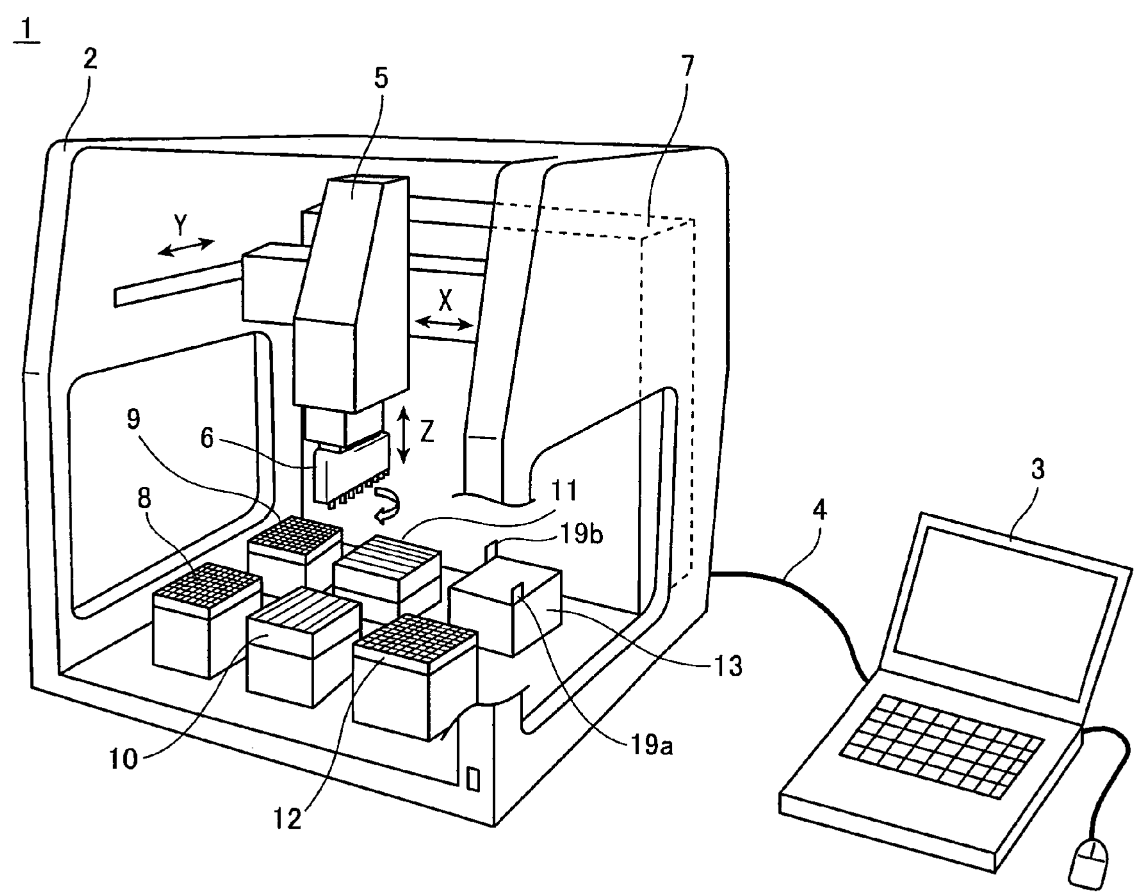
FIG. 1 is a perspective view showing an automatic dispenser according to a preferred embodiment.

An automatic dispenser according to the preferred embodiment of the invention will be described with reference to the accompanying drawings. FIG. 1 is a perspective view showing an automatic dispenser 1 according to the preferred embodiment. The automatic dispenser 1 includes an outer casing 2, a controller 3, and a communication cable 4.

The outer casing 2 accommodates a transporter 5, a dispensing head 6, a circuit section 7, dispensing tip vessels 8 and 9, reagent vessels 10 and 11, a microplate 12, and a disposal vessel 13. The dispensing tip vessel 8, reagent vessel 10, and microplate 12 are arranged in a row within the outer casing 2 parallel to another row formed by the dispensing tip vessel 9, reagent vessel 11, and disposal vessel 13. The gap between the disposal vessel 13 and the microplate 12 is wider than that between the disposal vessel 13 and the reagent vessel 11. In the preferred embodiment, the direction in which the dispensing tip vessel 8, reagent vessel 10, and microplate 12 are arranged in that order will be referred to as the positive direction along the X-axis. The direction from the disposal vessel 13 to the microplate 12 that is orthogonal to the X-axis will be referred to as the positive direction along the Y-axis. With respect to the move of the dispensing head 6, the direction which the dispensing head 6 moves upwards will be referred to as the negative direction and the direction which the dispensing head 6 moves downwards will be referred to as the positive direction along the Z-axis orthogonal to both the X-axis and Y-axis.

Stepping motors (not shown) are provided for driving the transporter 5 along the X-axis, Y-axis, and Z-axis. The dispensing head 6 is disposed on the bottom end of the transporter 5 and includes twelve syringes 1*a*-12*a* (see, for example, FIG. 4(*a*)) that are arranged in a row. Each syringe can accommodate one dispensing tip 14, with the gap between adjacent syringes being 9 mm. Further, since a dispensing head 6 is capable of rotating 90 degrees between the X-axis and Y-axis, a dispensing operation can be performed along either the X or Y direction. The circuit section 7 is provided with a driving circuit for driving the transporter 5 to X-direction, Y-direction, and Z-direction based on conditions inputted via the controller 3, an output circuit for outputting signals from sensors to the controller 3, and microprocessor (CPU).

The dispensing tip vessels 8 and 9 are provided with wells at intervals of 9 mm for accommodating the dispensing tips 14. The dispensing tips 14 are mounted in the dispensing head 6 and serve as vessels for temporarily storing reagent. The reagent vessels 10 and 11 accommodate reagent that the dispensing head 6 draws into the dispensing tips 14. Ninety-six wells are formed in the microplate 12 in a grid shape having eight wells longitudinally (along the Y-axis) and twelve wells latitudinally (along the X-axis) at intervals of 9 mm. The reagent accommodated in the dispensing tips 14 is ejected into the wells of the microplate 12.

Figure 2:
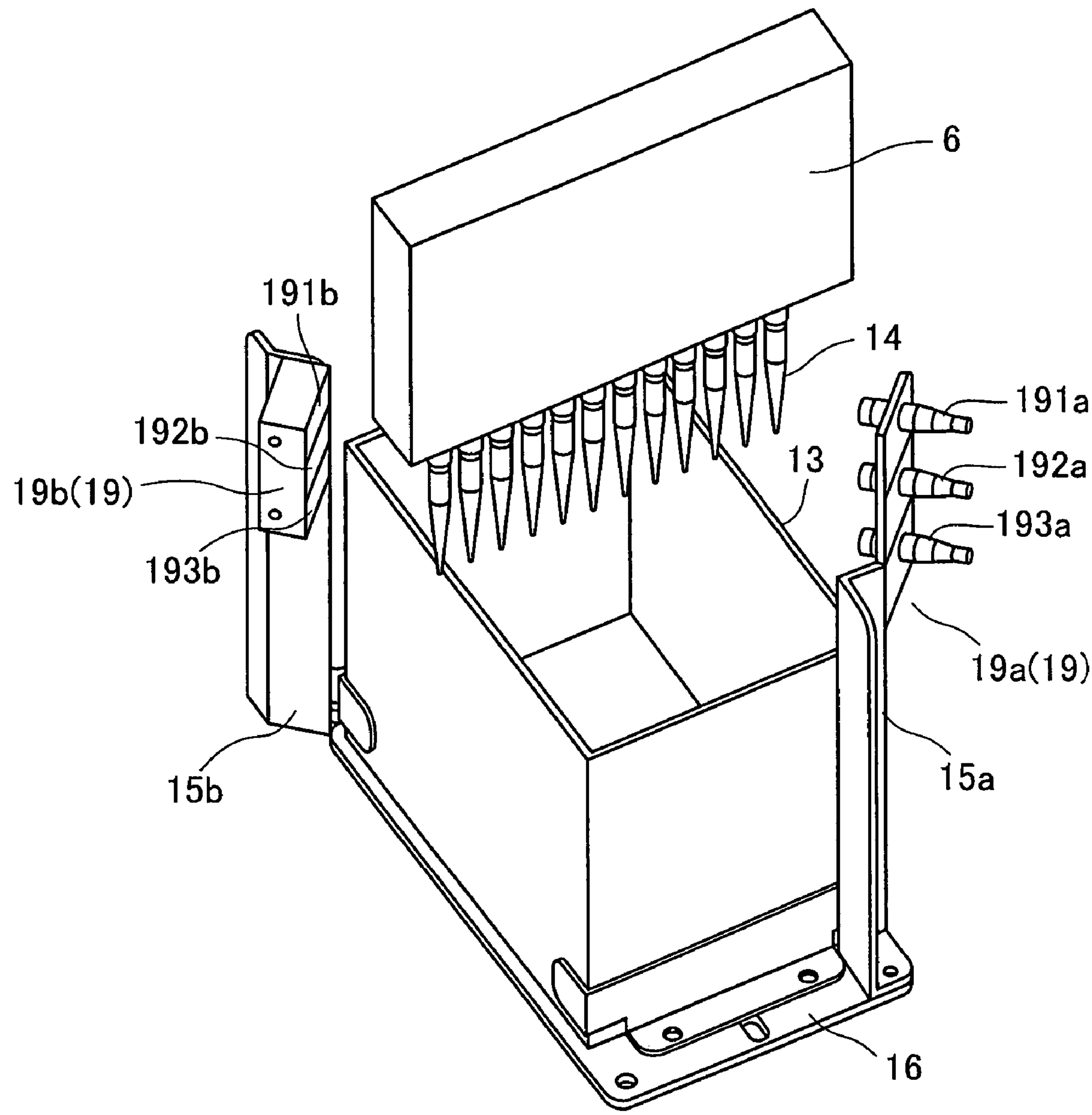
FIG. 2 is a perspective view showing a disposal vessel provided with dispensing tip sensors according to the preferred embodiment.

FIG. 2 is a perspective view showing the disposal vessel 13 provided with the dispensing tip sensors 19*a* and 19*b* according to the preferred embodiment. The disposal vessel 13 is provided for discarding used dispensing tips 14. The disposal vessel 13 is provided with dispensing tip sensors 19*a* and 19*b*. The dispensing tip sensors 19*a* and 19*b* can detect the existence and mounting states of a dispensing tip 14 in the dispensing head 6. The disposal vessel 13 is a rectangular parallelepiped constructed of walls that are parallel to each of the X-, Y-, and Z-axes. The dispensing tip sensors 19*a* and 19*b* are disposed on the top part of the disposal vessel 13. Specifically, the dispensing tip sensors 19*a* and 19*b* are mounted on support members 15*a* and 15*b*, respectively, that are fixed to a base 16, and the base 16 is in turn fixed to the outer casing 2.

The dispensing tip sensor 19*a* includes light emitting/receiving elements 191*a*, 192*a*, and 193*a*, and the dispensing tip sensor 19*b* includes reflecting plates 191*b*, 192*b*, and 193*b*. The light emitting/receiving elements 191*a*, 192*a*, and 193*a* are arranged in order from top to bottom along the Z-axis above one corner of the disposal vessel 13. The reflecting plates 191*b*, 192*b*, and 193*b* are similarly arranged above another corner of the disposal vessel 13 diagonally opposed to the first corner, so that the light emitting/receiving element 191*a* opposes the reflecting plate 191*b*, the light emitting/receiving element 192*a* opposes the reflecting plate 192*b*, and the light emitting/receiving element 193*a* opposes the reflecting plate 193*b*. Hence, light emitted from the light emitting/receiving element 191*a* is reflected off the reflecting plate 191*b* and returned to the light emitting/receiving element 191*a*. This process also holds true for the light emitting/receiving element 192*a* and reflecting plate 192*b*, and for the light emitting/receiving element 193*a* and reflecting plate 193*b*. Data detected by the dispensing tip sensors 19*a* and 19*b* is transmitted to the controller 3. Hereinafter, the light emitting/receiving elements 191*a*, 192*a*, 193*a* and the reflecting plate 191*b*, 192*b*, 193*b* will collectively be referred to as the "dispensing tip sensors 19".

Figure 3:
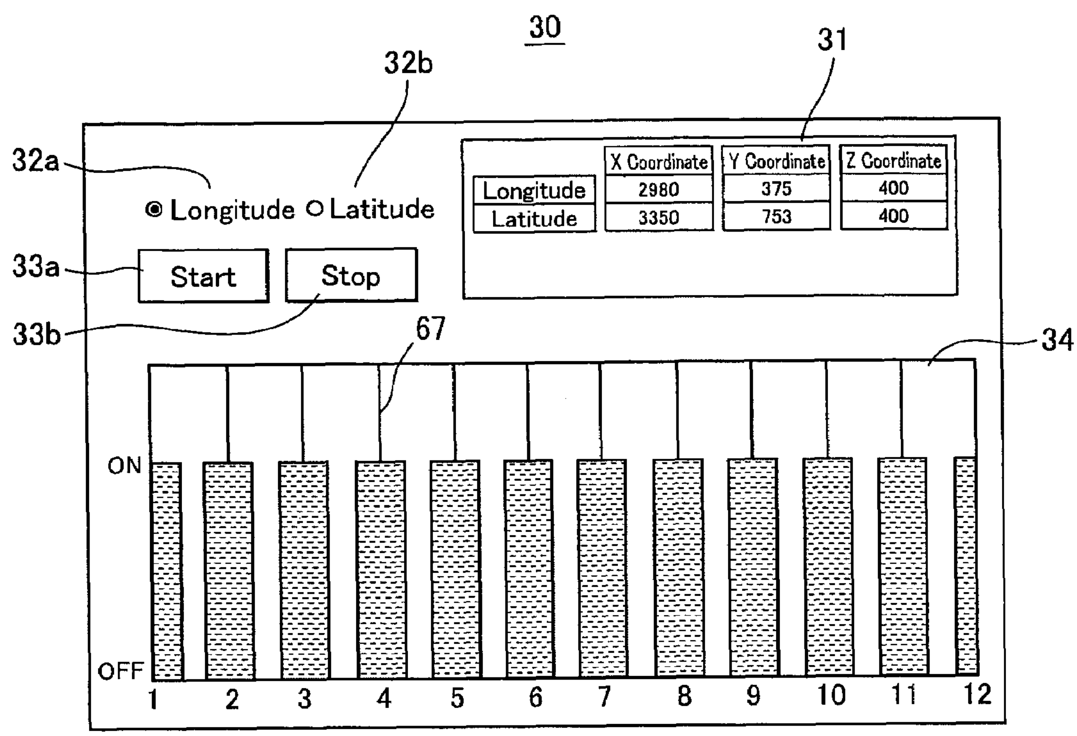
FIG. 3 is an explanatory diagram showing an adjustment/detection window according to the preferred embodiment.

The controller 3 is a general-purpose personal computer connected to the outer casing 2 by the communication cable 4 for a local area network (LAN), for example. The controller 3 displays an adjustment/detection window 30 (see FIG. 3) for adjusting the reference position of the dispensing head 6 in the XY plane and outputting the result of detecting the mounting states of the dispensing tips 14. As shown in FIG. 3, the adjustment/detection window 30 includes input spaces 31 for inputting X, Y, and Z coordinates, a longitude selecting button 32*a*, a latitude selecting button 32*b*, a detection start button 33*a*, a detection stop button 33*b*, and a waveform window 34.

The detection starting position for beginning detections of the dispensing tips 14 is set in the input spaces 31. The longitude selecting button 32*a* sets the orientation of the dispensing head 6 in the longitudinal direction, which is equivalent to the Y direction. The latitude selecting button 32*b* sets the orientation of the dispensing head 6 in the latitudinal direction, which is equivalent to the X direction. The detection start button 33*a* is selected to begin moving the dispensing head 6, while the detection stop button 33*b* is selected to stop movement of the dispensing head 6. Results of detection by the dispensing tip sensors 19 are displayed in the waveform window 34 as waveforms.

The controller 3 is also provided with various functions not shown in the drawings, including a waveform converting unit, a calibrating unit, a dispensing tip sensor adjustment displaying unit, a dispensing tip adjustment displaying unit, a storage unit, a dispensing process inputting unit, and a detection timer. The waveform converting unit converts data transmitted from the dispensing tip sensors 19 into a signal waveform that can be displayed in the waveform window 34. The calibrating unit automatically overwrites coordinate data set in the input spaces 31 by the adjusted coordinate data obtained through an adjustment operation to be described hereinafter. The dispensing tip sensor adjustment displaying unit displays a message prompting the user to adjust the dispensing tip sensors 19. The storage unit can store in advance a desired waveform achieved when a proper dispensing tip 14 is correctly mounted in the dispensing head 6. The dispensing tip adjustment displaying unit displays a message prompting the user to remount the dispensing tip if the tip has not been mounted properly or if the mounted tip is an incorrect type. The dispensing process inputting unit enables the user to input a desired dispensing process, whereafter the automatic dispenser automatically executes the inputted dispensing process. The detection timer measures the time elapsed in waveform converting operation to be described hereinafter.

X, Y, and Z coordinates for the starting point and ending point of movement must be stored in the controller 3 in advance in order to control the transporter 5 to move the dispensing head 6 to the desired position designated by the ending point. Accordingly, the input spaces 31 enable the user to enter the detection starting position for detecting the dispensing tip 14 for each orientation of the dispensing head 6. Values in the input spaces 31 are displayed as absolute coordinates from the origin points on each of the X-, Y-, and Z-axes and are set in 0.1 mm increments. For example, the value "2980" written as the X coordinate for the longitudinal direction in FIG. 3 indicates that the detection starting position is 298.0 mm from the point of origin on the X-axis. Since theoretical values to be inputted into the input spaces 31 are already known based on the dimensions of the transporter 5, dispensing head 6, dispensing tip sensor 19, and the like, these theoretical values may be set in the controller 3 as initial values.

Figure 4A:
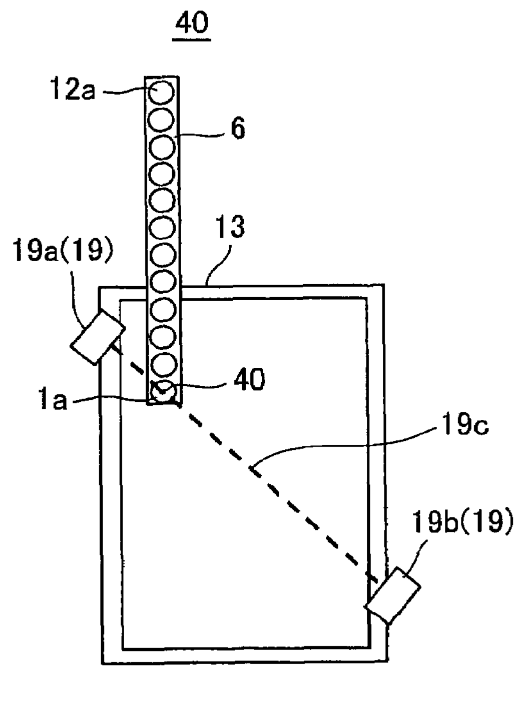
FIG. 4(*a*) is an explanatory diagram showing the detection starting position when the dispensing head is oriented longitudinally.
Figure 4B:
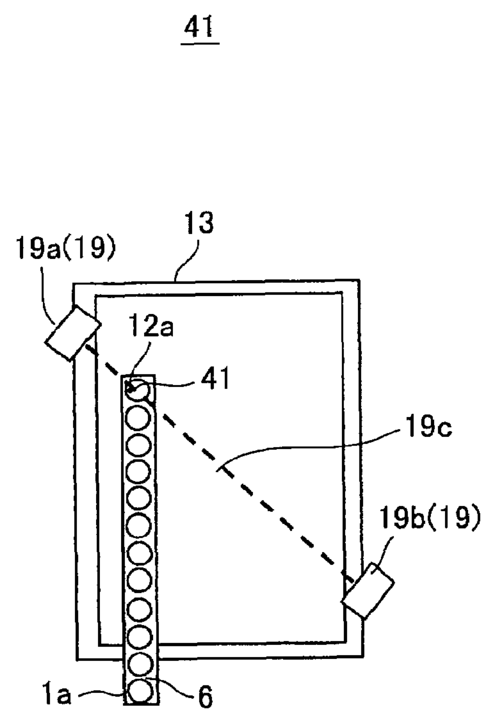

Next, operations for detecting the shape and mounting states of the dispensing tips 14 will be described. After the dispensing tips 14 are mounted in the syringes of the dispensing head 6, the user selects the orientation for the dispensing head 6 in the adjustment/detection window 30. Next, the theoretical value of the X, Y, and Z coordinates of detection starting position that has been stored in the controller 3 in advance is displayed in the input spaces 31. FIG. 4(*a*) shows the detection starting position and FIG. 4(*b*) the detection ending position for the dispensing head 6 when the orientation of the dispensing head 6 is longitudinal. In this example, the position at which the dispensing tip 14 mounted in the syringe 1*a* of the dispensing head 6 blocks an optical path 19*c* of the dispensing tip sensors 19 is a detection starting position 40 for the longitudinally oriented dispensing head 6. Therefore, the theoretical value of the X, Y, and Z coordinates of detection starting position 40 that has been stored in the controller 3 in advance is displayed in the input spaces 31.

Figure 5A:
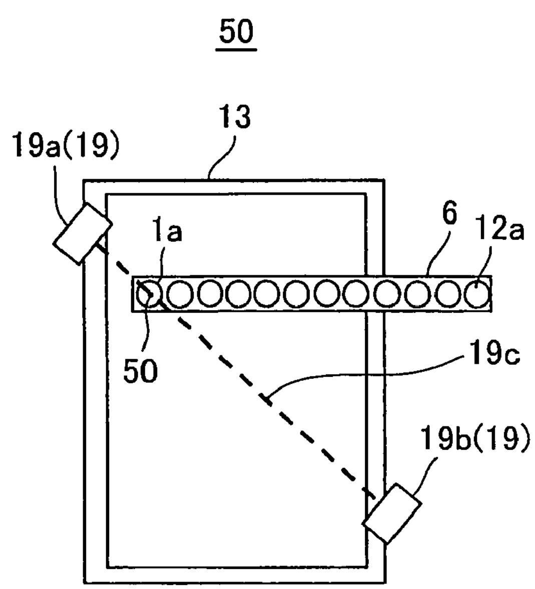
FIG. 5(*a*) is an explanatory diagram showing the detection starting position when the dispensing head is oriented latitudinally.
Figure 5B:
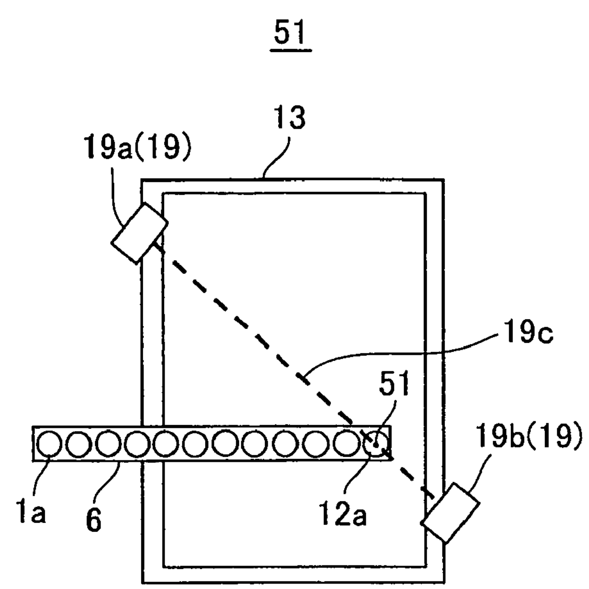
Figure 6A:
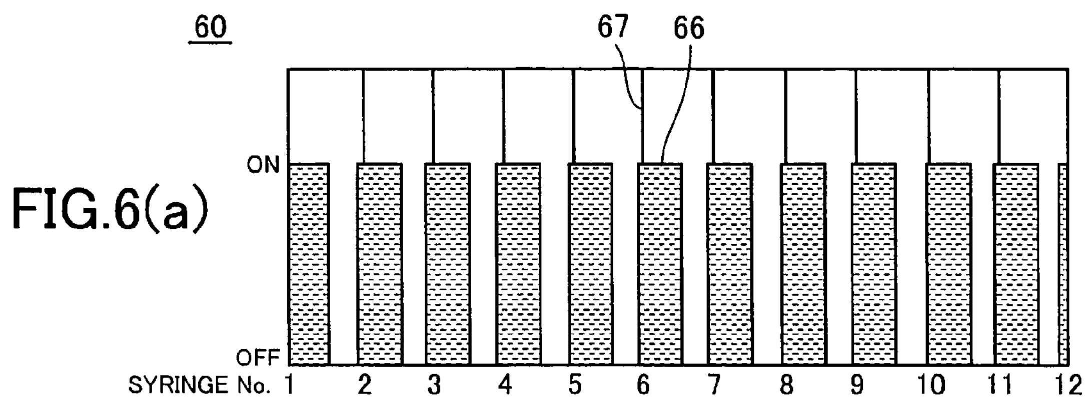
FIG. 6(*a*) is an explanatory diagram showing an example of a signal waveform displayed in a waveform window.
Figure 6B:
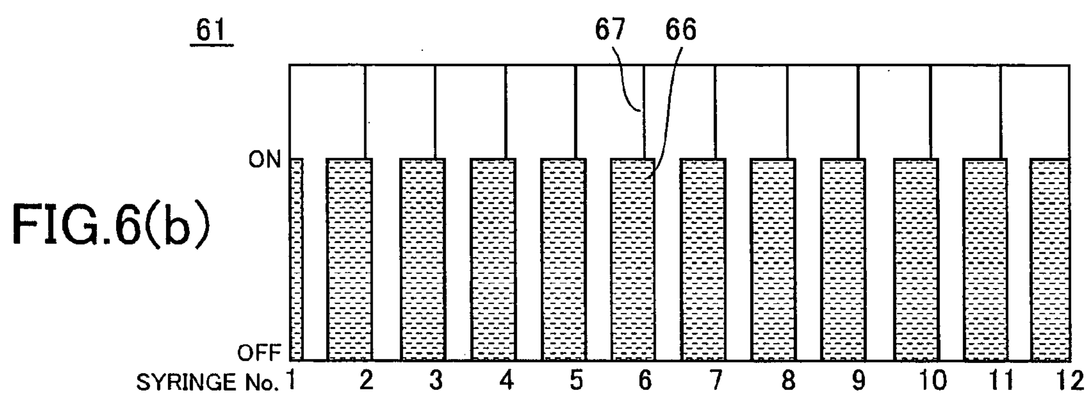
Figure 6C:
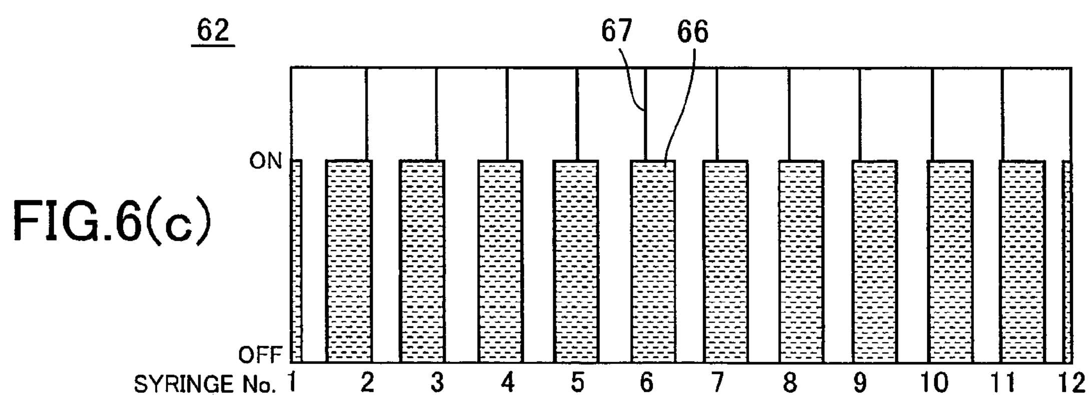
Figure 6D:
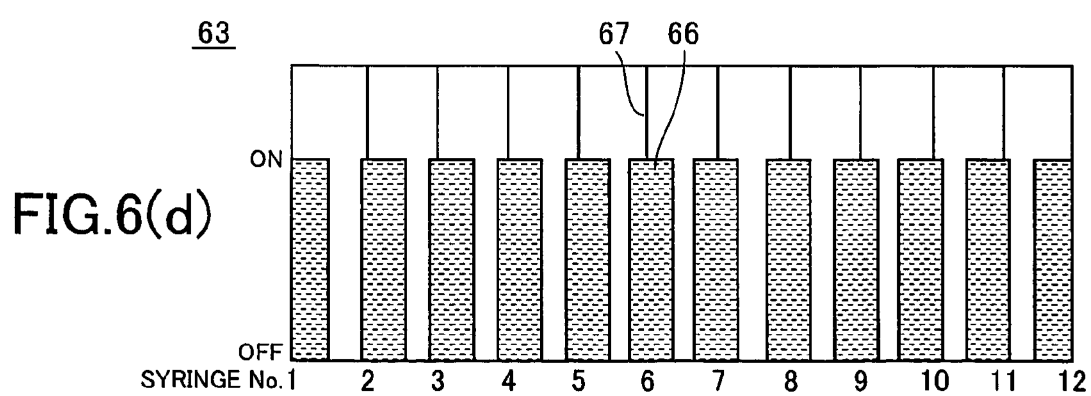

FIG. 5(*a*) shows the detection starting position and FIG. 5(*b*) the detection ending position when the dispensing head 6 is oriented latitudinally. In this case, the position at which the dispensing tip 14 mounted in the syringe 1*a* of the dispensing head 6 blocks the optical path 19*c* of the dispensing tip sensors 19 is a detection starting position 50 for the latitudinally oriented dispensing head 6. Accordingly, the theoretical value of the X, Y, and Z coordinates of detection starting position 50 that has been stored in the controller in advance is displayed in the input spaces 31. In addition, the theoretical value of the X, Y, and Z coordinates for the each detection starting position can be inputted into the input spaces 31 manually.

Next, the user selects the detection start button 33*a* to begin detection. If the user wishes to quit at any time during the detection process, the user can press the detection stop button 33*b*. After selecting the detection start button 33*a*, the transporter 5 begins moving the dispensing head 6 toward the coordinate position inputted in the input spaces 31 for either the longitudinal or latitudinal direction. That is, the transporter 5 moves the dispensing head 6 to the detection starting position 40 for the longitudinal orientation shown in FIG. 4(*a*) or the detection starting position 50 for the latitudinal orientation shown in FIG. 5(*a*).

At this time, the dispensing tips 14 mounted in the dispensing head 6 are moved along with the dispensing head 6. Using the example of detection with the light emitting/receiving element 191*a* and reflecting plate 191*b*, light emitted from the light emitting/receiving element 191*a* does not reach the reflecting plate 191*b* if the dispensing tip 14 is positioned on the optical path 19*c* connecting the light emitting/receiving element 191*a* and reflecting plate 191*b*, because the light is blocked by the dispensing tip 14. Accordingly, the light is not reflected by the reflecting plate 191*b*, and the light emitting/receiving element 191*a* does not receive reflected light. However, if the dispensing head 6 is positioned so that a gap between adjacent dispensing tips 14 is positioned on the optical path 19*c*, then light emitted from the light emitting/receiving element 191*a* reaches and is reflected off the reflecting plate 191*b*. Hence, the light emitting/receiving element 191*a* can receive the reflected light. This same process of detection holds true for the light emitting/receiving element 192*a* and reflecting plate 192*b* and for the light emitting/receiving element 193*a* and reflecting plate 193*b*.

Since the light emitting/receiving element 191*a* and reflecting plate 191*b*, the light emitting/receiving element 192*a* and reflecting plate 192*b*, and the light emitting/receiving element 193*a* and reflecting plate 193*b* are provided near opposing corners of the disposal vessel 13, the optical path 19*c* extending between these pairs of elements forms an angle with the dispensing head 6, regardless of whether the dispensing head 6 is oriented longitudinally or latitudinally. In the preferred embodiment, this angle is set to 45 degrees. Hence, each of the dispensing tips 14 can be made to intersect the optical path 19*c* one at a time sequentially by moving the dispensing head 6, regardless of the orientation of the dispensing head 6. After the dispensing head 6 is moved to the detection starting position 40 in the longitudinal orientation, the dispensing tip sensors 19 first detect the dispensing tip 14 mounted in the syringe 1*a* and transmit data for light transmitted by the light emitting/receiving element 191*a*, light emitting/receiving element 192*a*, and light emitting/receiving element 193*a* to the controller 3. After data for the dispensing tip 14 mounted in the syringe 1*a* is transmitted to the controller 3, the dispensing head 6 is moved to a position that enables the dispensing tip sensors 19 to detect the dispensing tip 14 mounted in the syringe 2*a*. In this way, the transporter 5 repeatedly moves the dispensing head 6 by intervals until the dispensing tip 14 mounted in the syringe 12*a* blocks the optical path 19*c*, that is, until the dispensing head 6 has been moved to a detection ending position 41 in the longitudinal direction.

The process is similar for the dispensing head 6 oriented latitudinally. That is, each dispensing tip 14 is detected sequentially as the dispensing head 6 is moved from the detection starting position 50 to a detection ending position 51. However, as described above, the gap between the disposal vessel 13 and the reagent vessel 11 is narrower than the gap between the disposal vessel 13 and the microplate 12. Accordingly, if the dispensing head 6 is moved linearly when the dispensing head 6 is oriented latitudinally, the dispensing tips 14 mounted in the dispensing head 6 will collide with the reagent vessel 11. For this reason, the dispensing head 6 is moved both in the X direction and in the Y direction when oriented latitudinally. Specifically, the dispensing head 6 is moved 49.5 mm with respect to both the X and Y coordinates. However, it is also possible to move the dispensing head 6 linearly in the latitudinal direction as well as the longitudinal direction if there are no obstructions in the outer casing 2 with respect to the direction of movement.

The signal transmitted to the controller 3 is converted into a waveform by the waveform converting unit. Specifically, the waveform converting unit converts the signal transmitted to the controller 3 into a waveform having a width equal to a period of an ON signal. The waveform window 34 displays this signal waveform. In FIG. 3, the positions where numbers 1 through 12 are indicated in the waveform window 34 correspond to center detection positions 67 (see FIG. 6) at which the correctly mounted dispensing tips 14 should be displayed. More specifically, the dispensing tip 14 mounted in the syringe 1*a* in FIG. 4(*a*) corresponds to the number 1 in the waveform window 34, while the dispensing tip 14 mounted in the syringe 12*a* in FIG. 4(*b*) corresponds to the number 12. The signal displayed in the waveform window 34 is ON when the dispensing tip 14 blocks the optical path 19*c* and OFF when the optical path 19*c* is not blocked.

Figure 13:
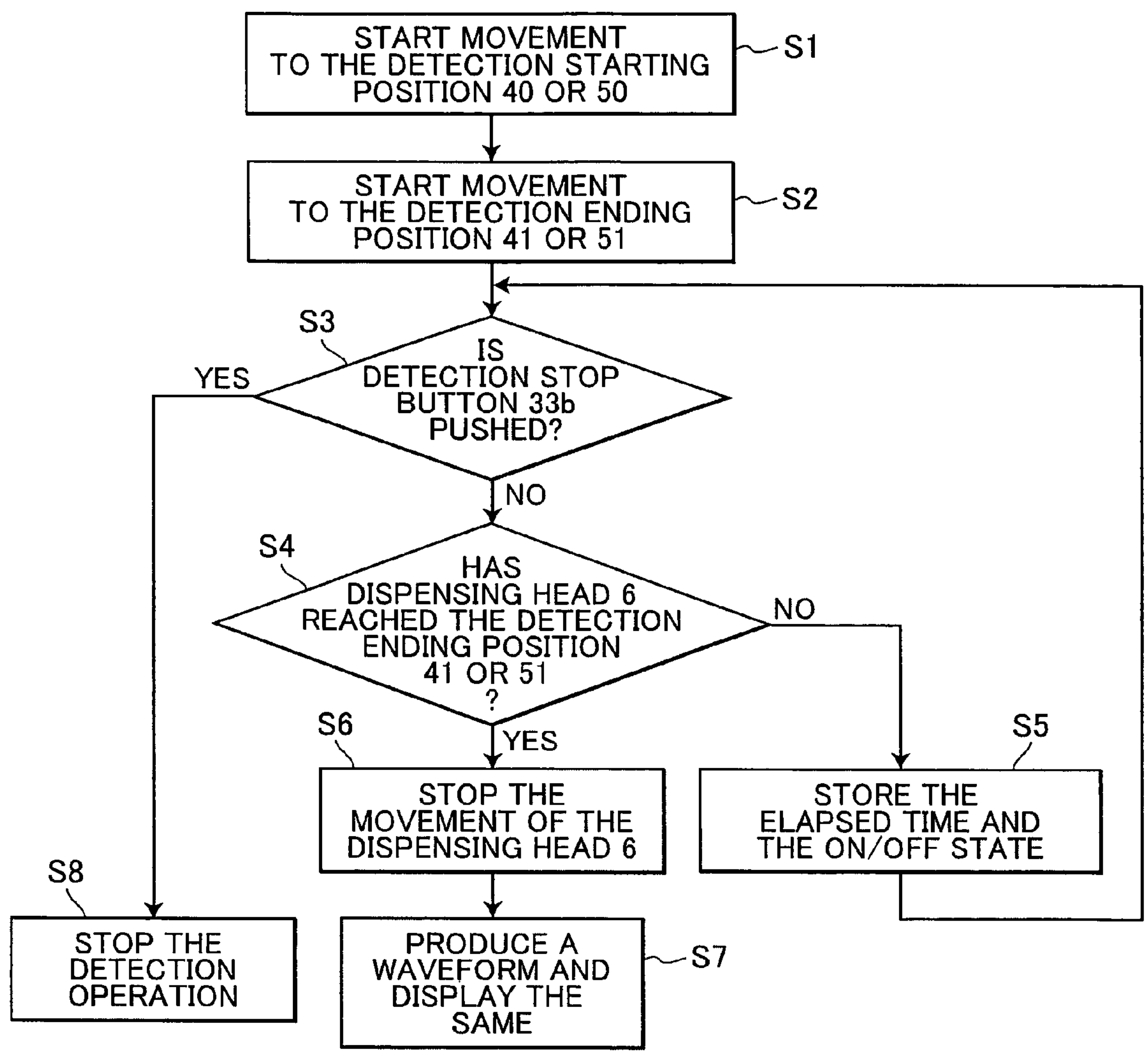
FIG. 13 is a flowchart illustrating a waveform display operation for displaying outputs from dispensing tip sensors.

The waveform converting operation will be described with reference to a flowchart shown in FIG. 13.

When either the longitude selecting button 32*a* or the latitude selecting button 32*b*, and the detection start button 33*a* are pushed, the dispensing head 6 starts moving to a predetermined detection starting position 40 or 50 (step 1). When the dispensing head 6 reaches the detection starting position 40 (or 50), the dispensing head 6 starts moving to the detection ending position 41 (or 51) at a constant speed. At this time, the detection timer starts measuring the elapsed time (step 2). When the dispensing head 6 starts moving to the detection ending position 41 (or 51) in step 2, the controller 3 starts monitoring whether the detection stop button 33*b* has been pushed or not (step 3). When the controller 3 determines that the detection stop button 33*b* has not been pushed in step 3 (step 3: NO), the controller 3 monitors whether the dispensing head 6 has reached the detection ending position 41 (or 51) (step 4). When the controller 3 determines that the dispensing head 6 has not yet reached the detection ending position 41 (or 51) (step 4: NO), the storage unit stores the elapsed time that has been measured by the detection timer and the ON/OFF state of the dispensing tip sensor 19 (step 5). Subsequently, the controller 3 returns to step 3 and repeats the operation that is performed in step 3 to step 5. When the controller 3 determines that the dispensing head 6 has reached the detection ending position 51 (step 4: YES), the dispensing head 6 stops moving (step 6). The waveform converting unit of the controller 3 produces a waveform whose horizontal-axis shows elapsed time and vertical-axis shows ON/OFF state of the dispensing tip sensor 19, and displays the waveform at waveform window 34 (step 7). When the controller 3 determines that the detection stop button 33*b* has been pushed in step 3 (step 3: YES), the dispensing head 6 stops moving (step 8).

If the reference position of the dispensing head 6 in the XY plane deviates from the reference of the dispensing tip sensors 19 in the XY plane at this time, the calibrating unit of the controller 3 automatically performs the adjustment operation to adjust the reference position of the dispensing head 6 by inputting the coordinate data set in the input spaces 31.

FIGS. 6(*a*)-6(*d*) show examples of signal waveforms displayed in the waveform window 34. For the simplicity of description, these drawings indicate only detection by one set of the dispensing tip sensors 19, such as the light emitting/receiving element 191*a* and the reflecting plate 191*b*.

Assuming the dispensing head 6 is oriented longitudinally, a state 60 shown in FIG. 6(*a*) in which the position of the twelve ON signals 66 are offset to the right of the center detection positions 67 signifies that the detection starting position 40 is offset toward the negative direction on the Y-axis. Accordingly, the detection starting position 40 must be shifted toward the positive side of the Y-axis. Since the gap between the center detection positions 67 is 9 mm, the amount in which the ON signals 66 are offset from the center detection positions 67 can easily be calculated. The controller 3 then completes adjustment of the dispensing tip detecting position by adding this amount of offset to the Y coordinate in the input spaces 31.

In contrast, FIG. 6(*b*) shows a state 61 in which the positions of the twelve ON signals 66 are offset toward the left with respect to the center detection positions 67, indicating that the detection starting position 40 is offset toward the positive side on the Y-axis. In this case, the controller 3 adjusts the dispensing tip detecting position by subtracting the amount of this offset from the Y coordinate in the input spaces 31. Here, the amount of offset between the dispensing tips 14 and the center detection positions 67 may differ according to the precision in which the dispensing tips 14 were manufactured. In such a case, the controller 3 may perform adjustments using an average value of offsets between each dispensing tip 14 and the corresponding center detection position 67.

Thus, the dispensing head 6 is accurately positioned by aligning the reference positions of the dispensing head 6 and the dispensing tip sensor 19. Therefore, the automatic dispenser 1 can detect the dispensing tip 14 accurately. Waveforms indicating the position of the dispensing tip 14 are displayed in the waveform display 34. Accordingly, the user can easily see how much the dispensing head 6 deviates from a prescribed position and, therefore, can easily correct this deviation. The controller 3 determines the shape and mounting states of the dispensing tips 14 by comparing a detected waveform with the model waveform, thereby more easily and reliably preventing errors in mounting the dispensing tip 14. Further, since the controller 3 automatically adjusts the reference position of the dispensing head 6 in the XY plane with respect to the reference position of the dispensing tip sensors 19 in the XY plane, less time and effort is required to adjust the dispensing head 6 in comparison with manual. A man may also adjust the reference position of the dispensing head 6 by inputting values in the input spaces 31 based on the waveform displayed in the waveform window 34 showing the positions of the dispensing tips 14.

Figure 14:
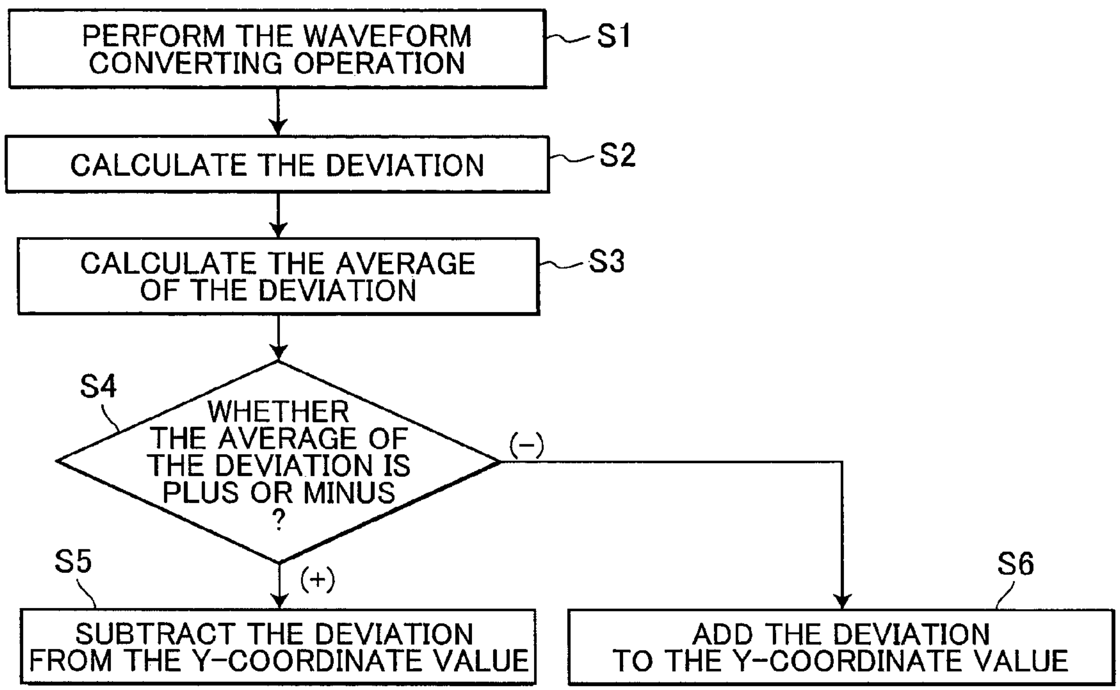
FIG. 14 is a flowchart illustrating a reference position adjustment operation along the Y-axis when the dispensing head is oriented in the longitudinal direction.

The reference position adjustment operation will be described with reference to a flowchart shown in FIG. 14. In the following description, it is assumed that the dispensing head 6 is oriented longitudinally. After the waveform converting operation described above is performed (step 1), the controller 3 calculates the offset between the center of the waveform of each dispensing tip and the center detection position 67 (step 2). The controller 3 calculates the average of the offset calculated at step 2 (step 3). The controller 3 then determines whether the average of the offset is positive (i.e., the dispensing head 6 is shifted in the positive direction on the Y-axis or the side of the syringe 12*a*) or negative (i.e., the dispensing head 6 is shifted in the negative direction on the Y-axis or the side of the syringe 1*a*) with respect to the center detection position 67 (step 4). When the controller 3 determines that the average of the offset is positive (+) in step 4, the calibrating unit subtracts the offset from the predetermined Y-coordinate value and stores the resultant value in the storage unit (step 5). When the controller 3 determines that the average of the offset is negative (−) in step 4, the calibrating unit adds the offset to the predetermined Y-coordinate value and stores the resultant value in storage unit (step 6).

However, as can be seen in FIGS. 5(*a*) and 5(*b*), when detecting the dispensing tip 14 for the latitudinally oriented dispensing head 6, the position at which the dispensing tip 14 blocks the optical path 19*c* does not remain fixed, but rather goes farther away from the light emitting/receiving element 191*a* as moving from the detection starting position 50 to the detection ending position 51. The angle formed by the optical path 19*c* and the X-axis is designed to be 45 degrees. Accordingly, the positions of the ON signals 66 with respect to the center detection positions 67 gradually move further toward the right in a state 62 shown in FIG. 6(*c*) or gradually to the left in a state 63 shown in FIG. 6(*d*) as progressing from number 1 to number 12, if the angle formed by the optical path 19*c* and the X-axis is not exactly 45 degrees. In such a case, it is necessary to adjust the mounting states of the light emitting/receiving element 191*a* and reflecting plate 191*b*.

With the state 62 shown in FIG. 6(*c*), the offset gradually moving to the right can be corrected by moving the light emitting/receiving element 191*a* in the counterclockwise direction of FIGS. 5(*a*) and 5(*b*). With the state 63 shown in FIG. 6(*d*), the offset gradually moving to the left can be corrected by moving the light emitting/receiving element 191*a* in the clockwise direction of FIGS. 5(*a*) and 5(*b*).

Figure 15:
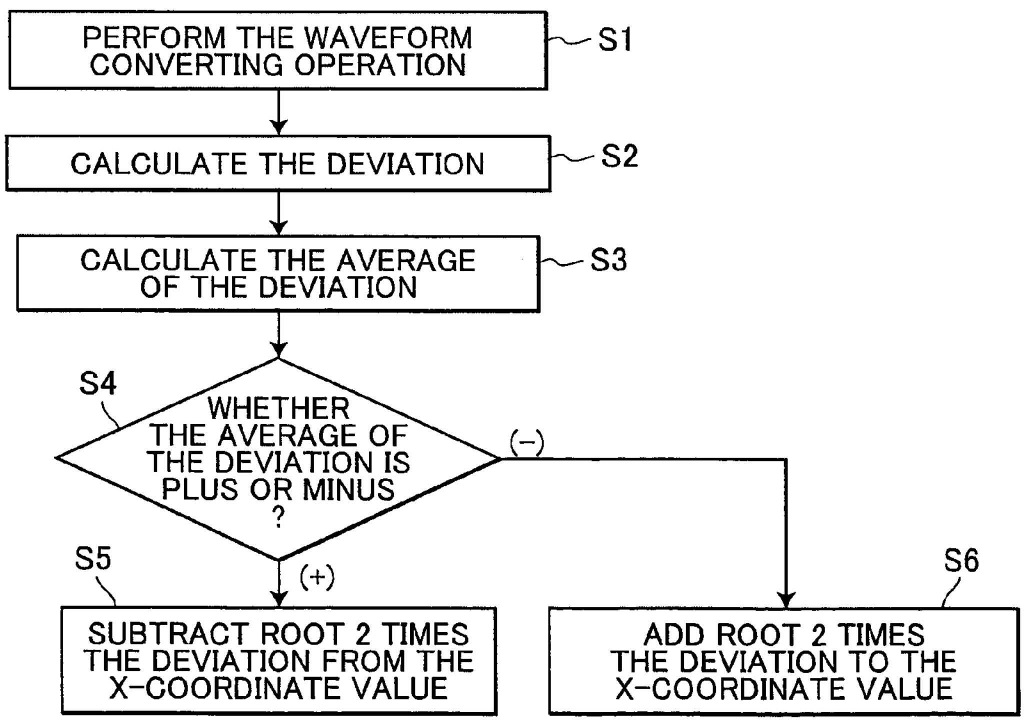
FIG. 15 is a flowchart illustrating a reference position adjustment operation along the X-axis when the dispensing head is oriented in the latitudinal direction.

The reference position adjustment operation will be described with reference to a flowchart shown in FIG. 15. In the following description, it is assumed that the dispensing head 6 is oriented latitudinally. After the waveform converting operation described above is performed (step 1), the controller 3 calculates the offset between the center of the waveform of each dispensing tip and the center detection position 67 (step 2). The controller 3 calculates the average of the offset calculated at step 2 (step 3). The controller 3 then determines whether the average of the offset is positive (i.e., the dispensing head 6 is shifted in the positive direction on the X-axis or the side of the syringe 12*a*) or negative (i.e., the dispensing head 6 is shifted in the negative direction on the Y-axis or the side of the syringe 1*a*) for the center detection position 67 (step 4). When the controller 3 determines that the average of the offset is positive (+) in step 4, the calibrating unit subtracts $\sqrt{2}$ (root 2) times the offset from the predetermined X-coordinate value and stores the resultant value in the storage unit (step 5). When the controller 3 determines that the average of the offset is negative (−) in step 4, the routine proceeds to step S6 where the calibrating unit adds $\sqrt{2}$ times the offset to the predetermined X-coordinate value and stores the resultant value in storage unit.

Further, when the base 16 is not fixed on the outer casing 2 accurately, the dispensing tip sensors 19 deviates from a predetermined position. In such a case, the dispensing tip sensor adjustment displaying unit displays a message indicating that the dispensing tip sensors 19 are out of position and prompts the user to adjust the dispensing tip sensors 19. Note that since the dispensing tip sensors are fixed on the support that is fixed on the base 16, the angle between the light emitting/receiving element 191*a*, 192*a*, 193*a* and the reflecting plate 191*b*, 192*b*, 193*b* does not deviate. Hence, by performing the adjustment according to the description in the adjustment displaying unit, the user can prevent detection problems caused by the dispensing tip sensors 19 themselves being out of position. Further, by setting the dispensing tip sensors 19 in the correct position, the position of the dispensing head 6 can be more accurately adjusted. Note that when the dispensing tip sensors 19 deviate from the predetermined positions, it is preferred that the reference position adjustment operation is performed again after the adjustment of the dispensing tip sensors 19. Hence, the automatic dispenser 1 performs reference position adjustment operations for the dispensing head 6 according to the procedure described above.

By providing the controller 3 with the dispensing process inputting unit, the user can input a desired process in this inputting unit, directing the automatic dispenser 1 to automatically perform a series of dispensing operations according to the details inputted into the controller 3. A common series of dispensing operations includes the sequence of mounting the dispensing tips 14, drawing reagent into the dispensing tips 14 from the reagent vessels 10 and 11, ejecting the reagent into the microplate 12, and discarding the dispensing tips 14 in the disposal vessel 13. By incorporating the adjustment operation described above in this series of dispensing operations, the controller 3 can perform the adjustment operation during the dispensing operation, automatically correcting the coordinates of the detection starting position 40 and detection starting position 50 if it is determined that these positions are not accurate.

With the automatic dispenser 1 according to this embodiment, the dispensing head 6 is accurately positioned by aligning the detection starting position for detecting the dispensing tips 14, that is, the reference positions of the dispensing head 6, thereby detecting the dispensing tips 14 accurately.

Figure 7A:
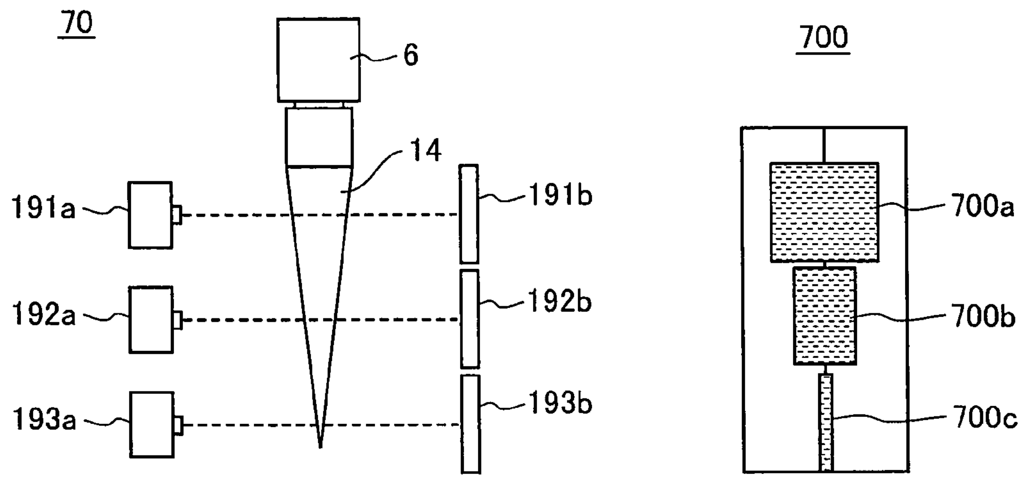
FIG. 7(*a*) is an explanatory diagram showing an example of a signal waveform displayed in a waveform window.
Figure 7B:
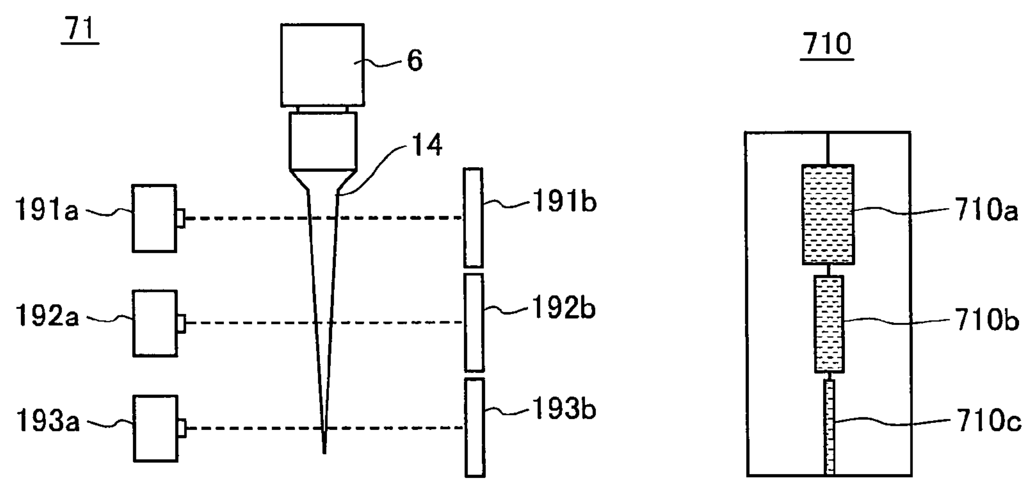
Figure 7C:
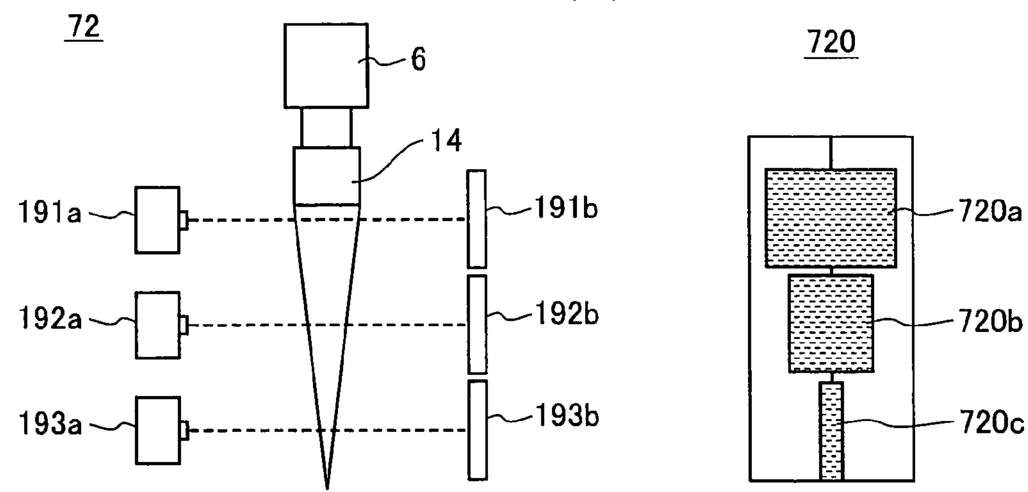
Figure 8A:
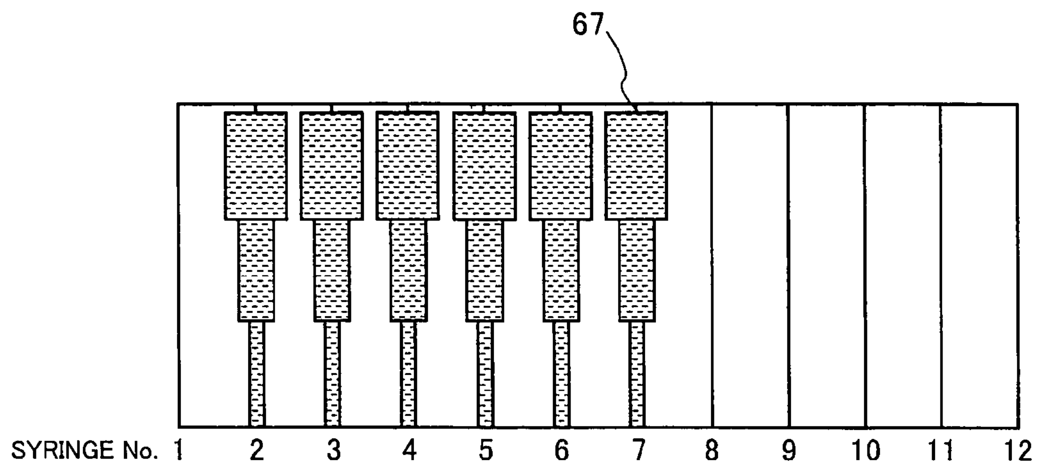
FIG. 8(*a*) is a explanatory diagram showing an example of a waveform window where a signal waveform is displayed.
Figure 8B:
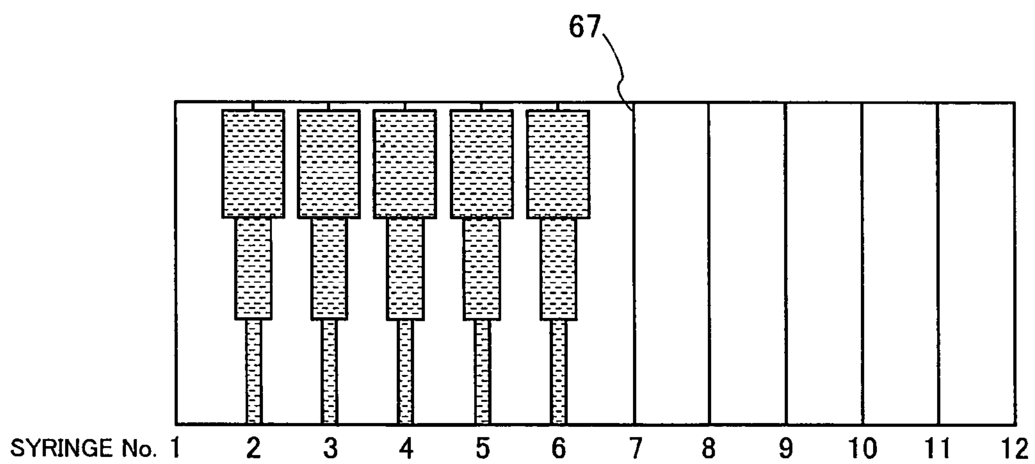
Figure 8C:
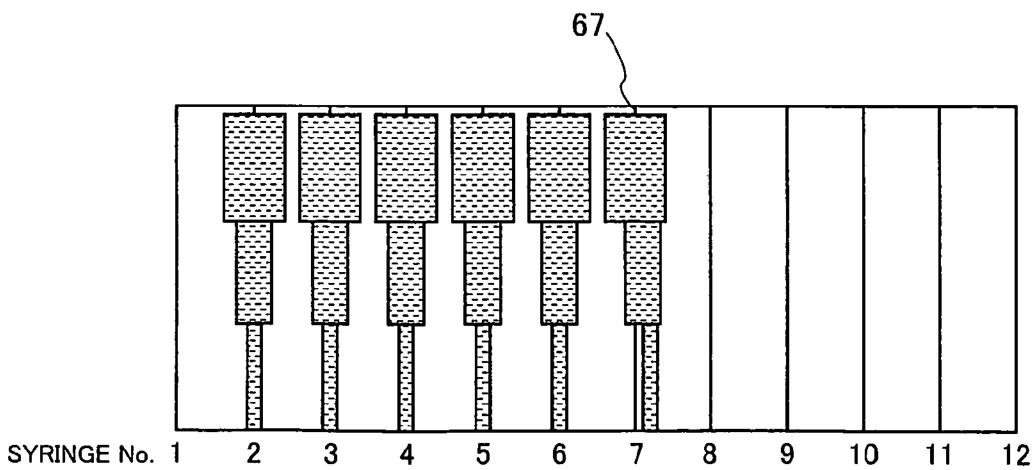
Figure 8D:
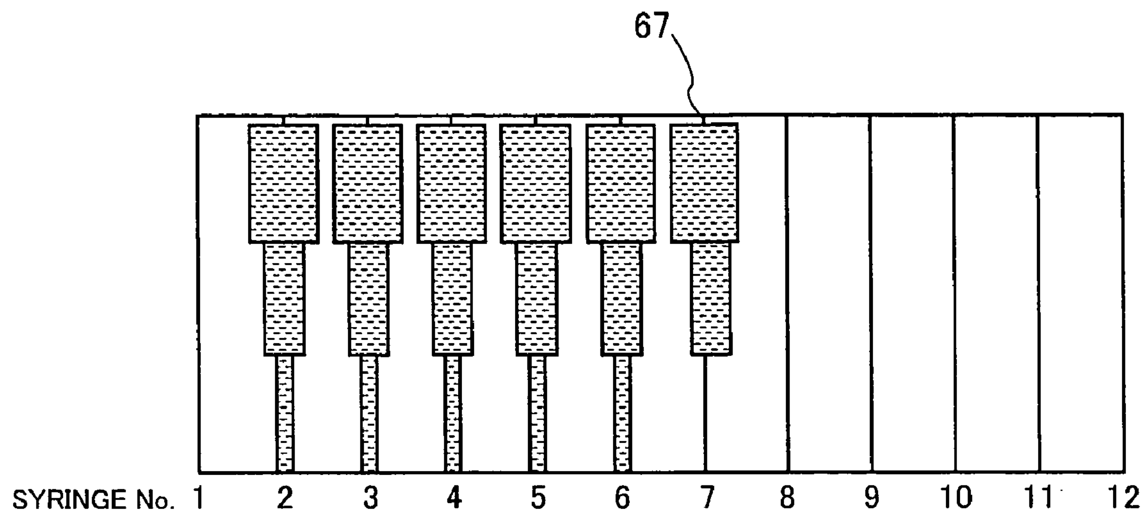
Figure 8E:
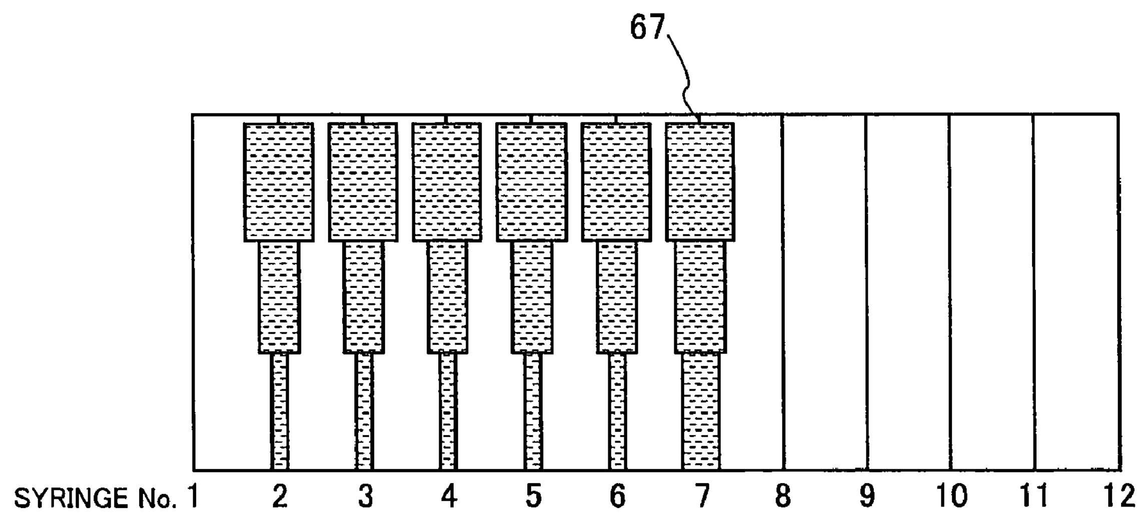

After completing the adjustment operation, the process returns to the detection operation. Here, the waveforms shown in FIGS. 6(*a*)-6(*d*) are actually displayed in the waveform window 34 in the form of a combination of waveforms detected by the three dispensing tip sensors 191*a*-193*a* and 191*b*-193*b*, as shown in FIGS. 7(*a*)-(*c*). FIG. 7(*a*) shows a signal waveform 700 for a state 70 in which a correct dispensing tip 14 is properly mounted. The signal waveform 700 includes a signal waveform 700*a* detected by the light emitting/receiving element 191*a*, a signal waveform 700*b* detected by the light emitting/receiving element 192*a*, and a signal waveform 700*c* detected by the light emitting/receiving element 193*a*, which are all displayed simultaneously. The signal waveform 700 is pre-stored in the storage unit of the controller 3. Waveforms indicating that a dispensing tip 14 has not been mounted are also stored in the storage unit when a dispensing tip 14 is intentionally not mounted in a syringe. If one or more of the three signal waveforms for the mounted dispensing tip are found to differ from the signal waveforms stored in the storage unit on comparison, an error message is displayed in the dispensing tip adjustment displaying unit of the controller 3. The displayed error message includes information indicating the syringe in which the abnormal dispensing tip is mounted and the waveforms for the tip.

FIG. 7(*b*) shows a signal waveform 710 for a state 71 in which a dispensing tip 140 having an abnormal shape is mounted. The signal waveform 710 includes a signal waveform 710*a* detected by the light emitting/receiving element 191*a*, a signal waveform 710*b* detected by the light emitting/receiving element 192*a*, and a signal waveform 710*c* detected by the light emitting/receiving element 193*a*, which are all displayed simultaneously.

When comparing the signal waveform 710 to the signal waveform 700, the width of the signal waveform 710*c* for the part near the end of the dispensing tip is found to be nearly identical to the signal waveform 700*c*. Therefore, it is difficult to determine a difference in shape based on only this comparison. However, the width of the signal waveform 710*a* near the base is clearly different from that of the signal waveform 700*a*. In this case, the controller 3 determines that the dispensing tip 14 mounted in the dispensing head 6 has a different shape, and displays an error message indicating this difference.

FIG. 7(*c*) shows a signal waveform 720 for a state 72 in which the mounted dispensing tip 14 is of a correct shape but is improperly mounted (the dispensing tip has not been firmly inserted into the dispensing head 6). When comparing the signal waveform 720 to the signal waveform 700, the widths of signal waveforms 720*a* near the base, 720*b* near the middle, and 720*c* near the end of the dispensing tip are greater than the corresponding signal waveforms 700*a*, 700*b*, and 700*c* at each position. In this case, the controller 3 determines that the dispensing tip 14 is not firmly inserted into the dispensing head 6, and displays an error message indicating this problem.

The detection operation is preferably performed not only after the dispensing tips are mounted in the dispensing head 6, but also after discarding the dispensing tips in the disposal vessel 13 following the dispensing operation. By performing the second operation, it is possible to determine whether the dispensing tips were reliably discarded in the disposal vessel 13, facilitating a smooth transition to the next dispensing operation.

Although only one signal waveform for one dispensing tip was described in FIGS. 7(*a*)-7(*c*), all waveforms for all dispensing tips are displayed in the waveform window 34.

FIGS. 8(*a*)-8(*d*) are explanatory diagrams showing examples of a waveform window 34 where signal waveforms are displayed.

FIG. 8(*a*) is an explanatory diagram showing an example of a normal waveform which has stored in a storage unit in advance. Numbers 1-12 correspond to the syringe 1*a*-12*a*, respectively. In the following description, it is assumed that the dispensing tips 14 are mounted only in syringes 2*a*-7*a* as shown in FIG. 8(*a*). The controller 3 compares a signal waveform detected actually with a normal signal waveform shown in FIG. 8(*a*) with respect to the presence of a dispensing tip on the center detection positions 67 and with respect to the shape of upper stand, middle stand, and lower stand of a dispensing tip.

In FIG. 8(*b*), nothing is displayed on number 7. In this case, controller 3 displays a message indicating that a dispensing tip is not mounted in syringe 7*a*. In FIG. 8(*c*), a signal waveform is not displayed on the center detection positions 67 of syringe 7*a* while displayed in the lower stand of the syringe 7*a*. In this case, controller 3 displays a message indicating that a different tip from a normal dispensing tip 14 is mounted on the syringe 7*a* or a dispensing tip is not mounted on the syringe 7*a* normally. In FIG. 8(*d*), a signal waveform is not displayed in the lower stand of the syringe 7*a*. In this case, controller 3 also displays a message indicating that a different tip from a normal dispensing tip 14 is mounted on the syringe 7*a* or a dispensing tip is not mounted on the syringe 7*a* normally. In FIG. 8(*e*), a waveform of middle and lower stands differ from a waveform of middle and lower stand in FIG. 8(*a*) while a waveform is respectively displayed on each stand of the syringe 7*a*. In this case, controller 3 also displays a message indicating that a different tip from a normal dispensing tip 14 is mounted on the syringe 7*a* or a dispensing tip is not mounted on the syringe 7*a* normally.

By comparing the detected signal waveforms to waveforms for a proper dispensing tip stored in the controller 3, the automatic dispenser 1 can determine both the shape and mounting states of the dispensing tips. Therefore, the automatic dispenser 1 can easily and reliably detect errors in the mounting states of the dispensing tips 14 in the dispensing head 6 and is prevented from driving with a dispensing tip improperly mounted. When mounting errors occur, the controller 3 displays an error message indicating the mounting error, enabling the user to prevent improperly mounted dispensing tips simply by remounting the dispensing tips according to the content of the error message. The waveform window 34 displays the waveform, thereby the shape and mounting states of the dispensing tips 14 are determined visually. Accordingly, the automatic dispenser 1 can reliably prevent errors in mounting the dispensing tip 14. Further, by detecting the dispensing tip at a plurality of locations, the shape and mounting states of the dispensing tips are determined based on signals for a plurality of locations, enabling a more reliable detection of mounting errors.

By incorporating this detection operation in a series of dispensing operations inputted in the dispensing process inputting unit, the controller 3 performs the detection operation during the dispensing operation and displays an error message when the dispensing tip is not perfectly mounted or when the mounted dispensing tip has a different shape.

Figure 9:
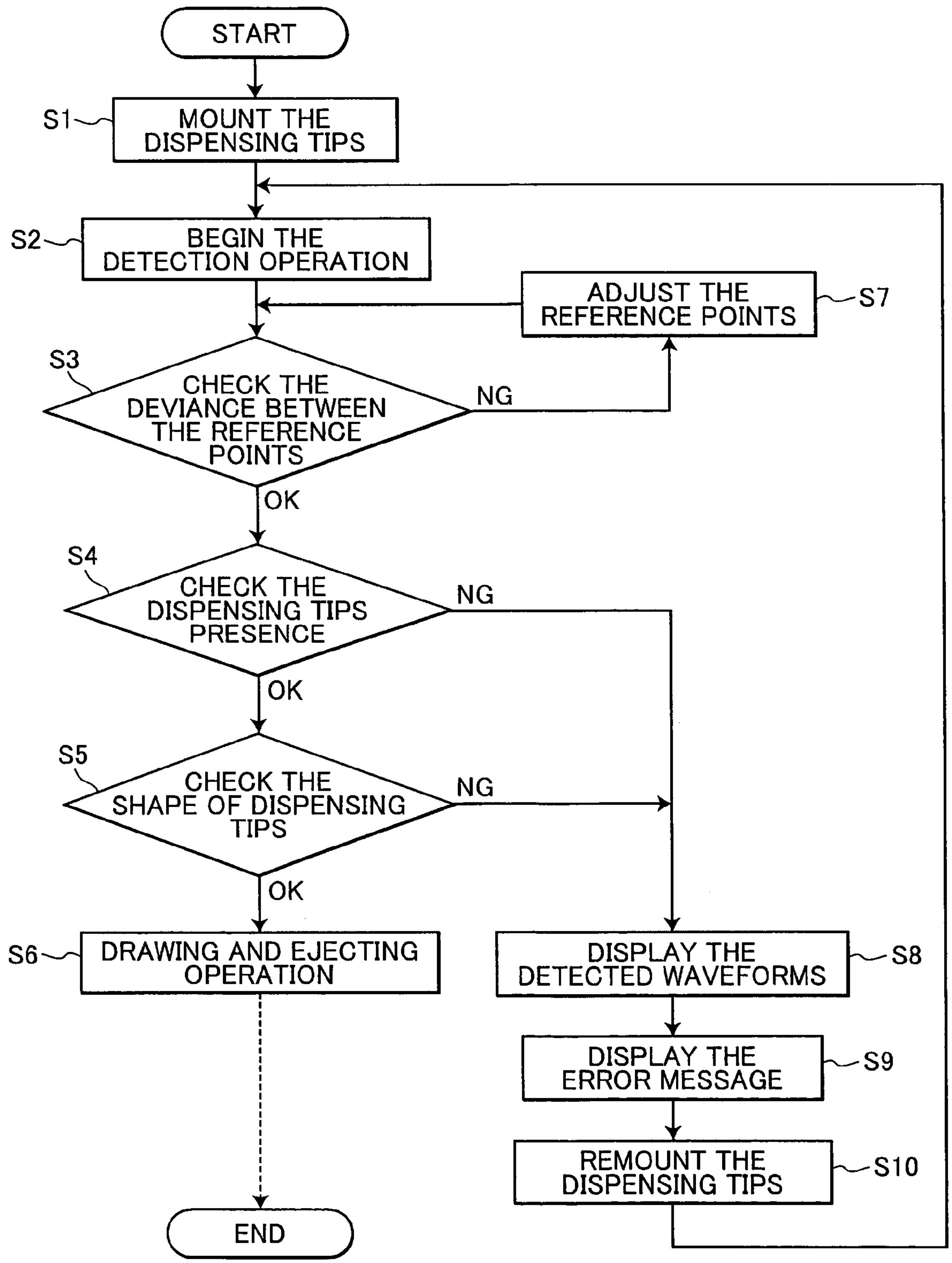
FIG. 9 is a flowchart showing the steps in an automatic dispensing process that incorporates a detection operation.

Next, an automatic dispensing process incorporating the adjustment/detection operations will be described with reference to the flowchart of FIG. 9. In step 1 the dispensing tips are mounted in the dispensing head 6. In step 2 the automatic dispenser 1 begins an operation to detect the dispensing tips. Data detected in step 2 is transmitted to the controller 3 and converted to signal waveforms by the waveform converting unit. In step 3 the controller 3 determines whether the reference position of the dispensing head 6 in the XY plane deviates from the reference position of the dispensing tip sensors 19 in the XY plane.

If there is any offset between the reference positions (step 3: NG), then in step 7 the controller 3 automatically adjusts the reference position of the dispensing head 6 in the XY plane and returns to step 3 to check for deviations between the reference position. If there is no offset between the reference position (step 3: OK), then in step 4 the controller 3 determines whether a dispensing tip is mounted in the dispensing head 6 based on the transmitted signal waveforms.

If the controller 3 determines that a dispensing tip is mounted in the dispensing head 6 (step 4: OK), then in step 5 the controller 3 determines whether the shape of the dispensing tip matches the shape of a proper dispensing tip 14. If the controller 3 determines that the shape of the dispensing tip matches the proper shape (step 5: OK), then in step 6 the automatic dispenser 1 begins the dispensing operation for drawing and ejecting reagent or the like.

However, if the controller 3 determines in step 4 that a dispensing tip is not mounted in the dispensing head 6 (step 4: NG) or if the controller 3 determines in step 5 that the shape of the dispensing tip does not match the proper shape (step 5: NG), then in step 8 the controller 3 displays the detected waveforms in the waveform window 34. In step 9 the controller 3 displays an error message in the dispensing tip adjustment displaying unit indicating the cause of the error. In step 10 the user remounts the dispensing tip 14 according to the error message displayed in the dispensing tip adjustment displaying unit. Subsequently, the operation for detecting the dispensing tip is repeated in step 2.

By incorporating this detection operation in the dispensing process inputting unit, the user can easily and reliably detect mounting errors and thereby avoid driving the automatic dispenser with a dispensing tip improperly mounted.

Figure 10:
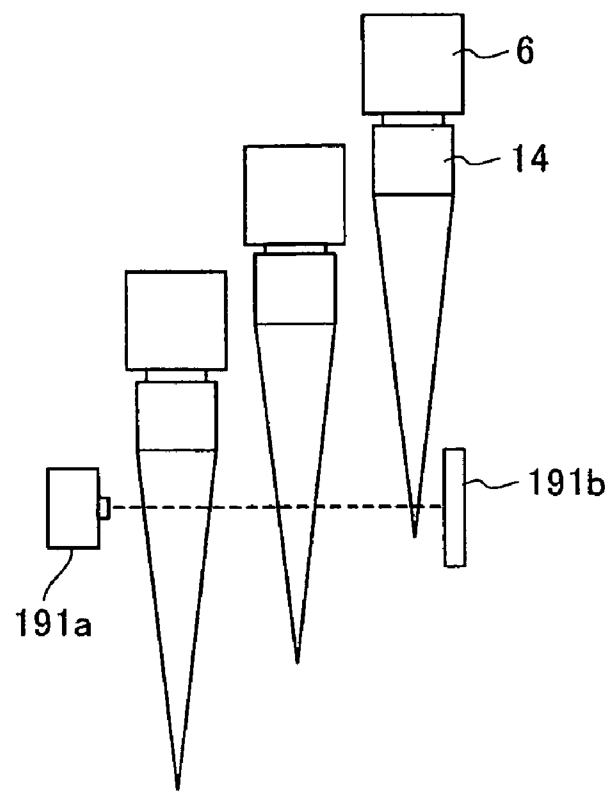
FIG. 10 is an explanatory diagram showing an example of an automatic dispenser that moves the dispensing tips through a detection position along a Z-axis and detects the dispensing tips at a plurality of locations with a set of dispensing tip sensors.

While the invention has been described in detail with reference to specific embodiments thereof, it would be apparent to those skilled in the art that many modifications and variations may be made therein without departing from the spirit of the invention, the scope of which is defined by the attached claims. For example, the precision for detection can be further increased by increasing the number of the dispensing tip sensors 19. Alternatively, it is possible to detect a dispensing tip in a plurality of locations using only one set of the dispensing tip sensors 19 that is configured of the light emitting/receiving element 191*a* and the reflecting plate 191*b* by moving the dispensing tip through the detection position in the Z direction, as shown in FIG. 10. In this configuration, the user can easily and reliably detect mounting errors and thereby avoid driving the automatic dispenser with a dispensing tip improperly mounted. Here, the dispensing tip can pass on the detection position in the X-Y direction. Thus, the user can more easily and reliably detect mounting errors and thereby avoid driving the automatic dispenser with a dispensing tip improperly mounted.

Figure 11:
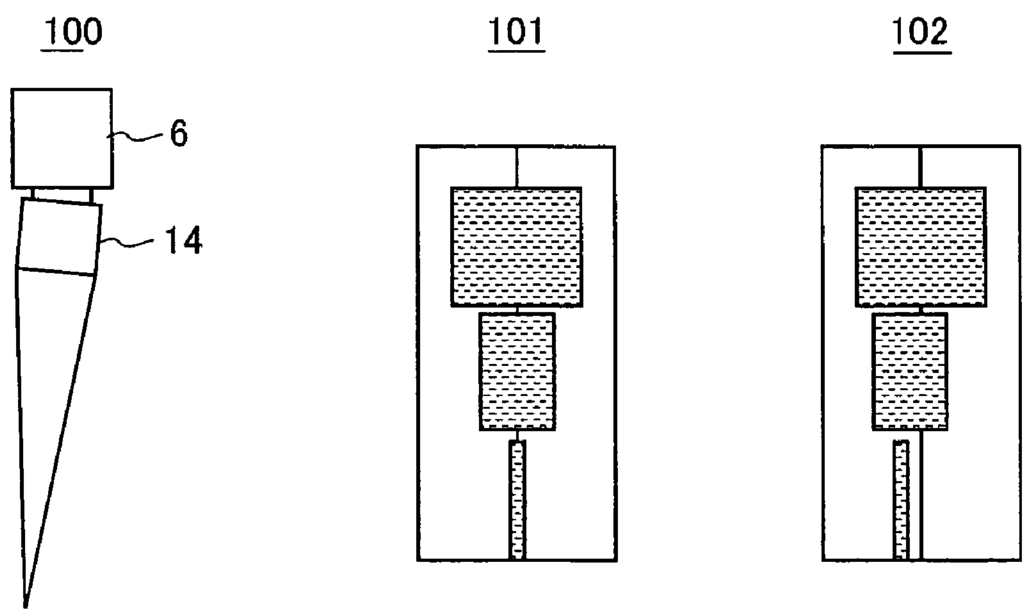
FIG. 11 is an explanatory diagram showing an example of an automatic dispenser that detects a dispensing tip from a plurality of directions.

It is also possible to detect a dispensing tip when the dispensing head 6 is oriented both longitudinally and latitudinally. FIG. 11 is an explanatory diagram of a dispensing tip mounted slanted with respect to the dispensing head 6. In a state 100 shown in FIG. 11, the dispensing tip may appear to be a proper dispensing tip 14 that is mounted correctly if the tip is detected in only one direction, as shown in a signal waveform 101. However, a difference can be detected by performing the detection from another direction, as illustrated in a signal waveform 102. By detecting the dispensing tip from a plurality of perspectives in this way, a three-dimensional shape of the dispensing tip can be acquired and mounting errors that are undetectable from one direction can be uncovered. Accordingly, the user can more easily and reliably detect mounting errors and thereby avoid driving the automatic dispenser with a dispensing tip improperly mounted.

In addition, the dispensing tip sensor 19 may detect the length of the dispensing tips in the Z direction, that is, the period when the dispensing tip 14 is located on the optical path 19*c* instead of detecting specific points of the dispensing tips. In this case, the detection starting position is set to a position 110 shown in FIG. 12, in which a part of the dispensing tip near the base blocks the optical path 19*c* when the dispensing tips are mounted in the dispensing head 6. Next, without changing the position of the dispensing head 6 in the XY plane, the dispensing head 6 is moved along the Z-axis in the negative direction to a detection ending position. The detection ending position is set as a position 111 at which the end of the dispensing tip 14 is farther toward the negative Z direction than the optical path 19*c*. Here, prescribed coordinates for the positions 110 and 111 may be inputted into the input spaces 31 in advance. In this case, a plurality of the dispensing tip sensor 19, for example, a number of the dispensing tip sensors 19 equal to the number of the dispensing tips 14 mounted on the dispensing head 6 can be mounted. Thus, the automatic dispenser 1 can reduce a time period required for detecting dispensing tips and detect dispensing tips efficiently. In addition, the detection of the length of dispensing tips may be performed not only in Z direction but also in X direction or Y direction.

Figure 12:
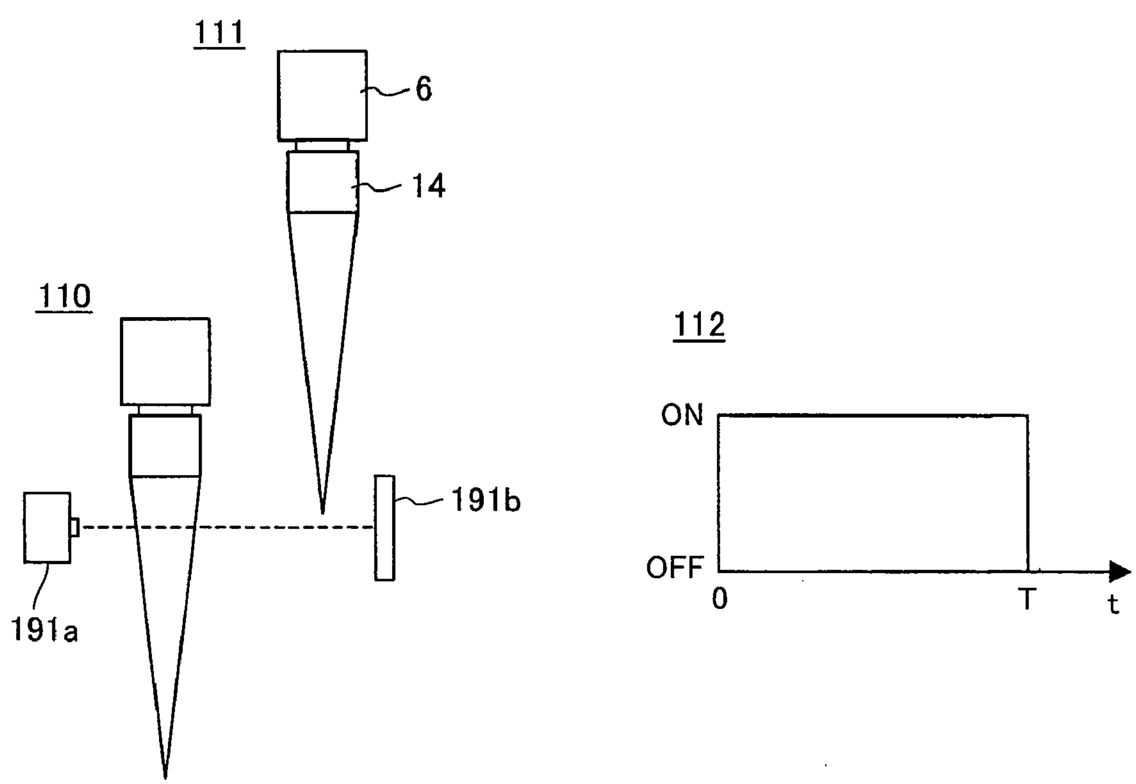
FIG. 12 is an explanatory diagram showing an example of an automatic dispenser that detects the length of the dispensing tips.

The dispensing tip sensors 19 continue detecting the dispensing tips while the transporter 5 moves the dispensing head 6 from the position 110 to the position 111. A graph 112 in FIG. 12 shows the detection signal during this time period. As shown in the graph 112, the end of the dispensing tip is moved to a position farther along the positive Z-axis than the optical path 19*c* in time T. The detected time T is compared to a time T0 that has been pre-stored in the controller 3 for the period in which the signal waveform is ON when a proper dispensing tip 14 is correctly mounted in the dispensing head 6. Since the time T is proportional to the length of the dispensing tip, it is possible to determine that a dispensing tip is not mounted correctly when the T0 and T differ. Accordingly, the automatic dispenser can reliably prevent errors in mounting the dispensing tips.

Further, the dispensing tip sensors may be configured so that one emits light and the other receives light. In the adjustment operation, the dispensing tip sensors may be configured to perform detection by ultrasound. Detection may also be performed in the detection operation using an area sensor. In this case, the results of this detection may be displayed after performing image processing. The dispensing tips may not also be disposed near opposing corners of the disposal vessel. The dispensing tip sensors need not be disposed above the disposal vessel, but can be provided anywhere that mounting is possible. The error message may be displayed by lighting an LED lamp or the like to notify the user of an abnormality. Not a plurality of dispensing tips but a single dispensing tip may be mounted on the dispensing head in detection.

What is claimed is:

1. An automatic dispenser comprising:

a dispensing head on which a plurality of dispensing tips is mountable;

a transporter that moves the dispensing head within an XYZ space defined by X-axis, Y-axis and Z-axis;

a controller that controls movement of the dispensing head by the transporter; and a sensor that detects the dispensing tips which move with the dispensing head from a detection starting point to a detecting ending point and generates a detection signal indicative of presence and absence of the dispensing tips, wherein the controller comprises a storage unit that stores X and Y coordinate values of the detection starting point and the detection ending point, a waveform converting unit that produces a detected waveform from the detection signal of the sensor, wherein the detected waveform has a horizontal axis which shows elapsed time that the dispensing head moves from the detection starting point to the detection ending point and a vertical axis which shows an ON/OFF signal indicative of presence and absence of the dispensing tips, and a calibrating unit that calculates an offset between the center of the detected waveform of each dispensing tip and a predetermined reference position and calibrates the X and Y coordinate values stored in the storage unit.

2. The automatic dispenser according to claim 1, wherein the storage unit stores a model waveform and the controller determines the shape and mounting states of the dispensing tips by comparing the detected waveform with the model waveform.

3. The automatic dispenser according to claim 1, wherein the dispensing head moves in the directions of the X-axis and the Y-axis, and the controller calibrates the Y-coordinate value when the dispensing head moves in the direction of the Y-axis.

4. The automatic dispenser according to claim 1, wherein a mounting state of the sensor is adjusted when the center positions of ON signals with respect to the predetermined reference positions gradually move to be delayed or advanced in time.

5. An automatic dispenser according to claim 1, wherein the controller comprises a storage unit that stores a model waveform, and determines a shape and mounting states of the dispensing tips by comparing the detection signal with the model waveform wherein the sensor comprises a plurality of the sensor elements that detect each of the dispensing tips at a plurality of locations, and wherein the controller includes means for comparing a plurality of signals for each of the dispensing tips detected by the plurality of sensor elements with a model waveform to determine whether the correct dispensing tips are mounted and whether each of the dispensing tips is correctly mounted.

6. The automatic dispenser according to claim 5, wherein the controller further comprises a dispensing tip adjustment display that prompts a user to remount a dispensing tip when the shape of the dispensing tip is not a prescribed shape or when the dispensing tip is not perfectly mounted.

7. The automatic dispenser according to claim 5, wherein the transporter moves the dispensing head so that the sensor can detect the dispensing tips at a plurality of locations, wherein the controller determines the shape and mounting states of the dispensing tips based on signals for a plurality of locations on the dispensing tips detected by the sensor.

8. The automatic dispenser according to claim 5, wherein the transporter comprises a head orientation changing device that changes an orientation of the dispensing head so that the sensor can detect a plurality of differing surfaces on the dispensing tips, wherein the controller determines the shape and mounted states of the dispensing tips based on signals for the plurality of surfaces of the dispensing tip detected by the sensor.

9. The automatic dispenser according to claim 5, wherein the controller further comprises a detected waveform display that generates a waveform based on the detection signal fed from the sensor and displays the waveform.

10. The automatic dispenser according to claim 5, wherein the model waveform indicates a predetermined ideal detection period, wherein the controller compares a detection period indicated by the waveform with the ideal detection period and determines the shape and mounting states of the dispensing tips.

* * * * *